(12) United States Patent
Zhou

(10) Patent No.: US 10,504,883 B2
(45) Date of Patent: Dec. 10, 2019

(54) METHOD FOR FABRICATING DAMASCENE STRUCTURE USING FLUOROCARBON FILM

(71) Applicants: SEMICONDUCTOR MANUFACTURING INTERNATIONAL (BEIJING) CORPORATION, Beijing (CN); SEMICONDUCTOR MANUFACTURING INTERNATIONAL (SHANGHAI) CORPORATION, Shanghai (CN)

(72) Inventor: Ming Zhou, Shanghai (CN)

(73) Assignees: SEMICONDUCTOR MANUFACTURING INTERNATIONAL (BEIJING) CORPORATION, Beijing (CN); SEMICONDUCTOR MANUFACTURING INTERNATIONAL (SHANGHAI) CORPORATION, Shanghai (CN)

( * ) Notice: Subject to any disclaimer, the term of this patent is extended or adjusted under 35 U.S.C. 154(b) by 0 days.

(21) Appl. No.: 15/720,734

(22) Filed: Sep. 29, 2017

(65) Prior Publication Data

US 2018/0175015 A1  Jun. 21, 2018

(30) Foreign Application Priority Data

Dec. 15, 2016 (CN) .......................... 2016 1 1156276

(51) Int. Cl.
*H01L 27/02* (2006.01)
*H01L 21/02* (2006.01)
(Continued)

(52) U.S. Cl.
CPC ...... *H01L 27/0207* (2013.01); *H01L 21/0212* (2013.01); *H01L 21/02074* (2013.01);
(Continued)

(58) Field of Classification Search
CPC ........... H01L 21/0212; H01L 21/31127; H01L 21/76811; H01L 21/76829; H01L 23/528; H01L 23/53295; H01L 27/0207
See application file for complete search history.

(56) References Cited

U.S. PATENT DOCUMENTS 6,207,585 B1 * 3/2001 Hasegawa ............. C23C 16/402
257/E21.243
6,599,838 B1 7/2003 Shih et al.
(Continued)

FOREIGN PATENT DOCUMENTS

JP 2007067324 3/2007
WO 03081645 10/2003

OTHER PUBLICATIONS

Ding et al., Spectral Characterization of Amorphous Fluorinated Carbon Film with a Low Dielectric Constant, Spectroscopy and Spectral Analysis, vol. 21, No. 6, http://www.cnki.net, Dec. 2001, pp. 745-748.
(Continued)

*Primary Examiner* — David C Spalla
(74) *Attorney, Agent, or Firm* — Kilpatrick Townsend & Stockton LLP

(57) ABSTRACT

A method for manufacturing an interconnect structure includes providing a metal interconnect layer, forming a dielectric layer on the metal interconnect layer, forming a fluorocarbon layer on the dielectric layer, forming a patterned hardmask layer on the fluorocarbon layer, etching the fluorocarbon layer and the dielectric layer using the patterned hardmask layer as a mask to form a trench in the
(Continued)

dielectric layer and a through-hole through the dielectric layer to the metal interconnect layer, forming a metal layer filling the trench and the through-hole, and planarizing the metal layer until the planarized metal layer has an upper surface that is flush with an upper surface of the fluorocarbon layer. The interconnect structure thus formed has an improved reliability.

14 Claims, 5 Drawing Sheets

(51) Int. Cl.
  | | |
  |---|---|
  | *H01L 21/311* | (2006.01) |
  | *H01L 23/528* | (2006.01) |
  | *H01L 23/532* | (2006.01) |
  | *H01L 21/768* | (2006.01) |
  | *C01B 21/082* | (2006.01) |
  | *C07F 7/08* | (2006.01) |

(52) U.S. Cl.
  CPC .. *H01L 21/31127* (2013.01); *H01L 21/76811* (2013.01); *H01L 21/76829* (2013.01); *H01L 23/528* (2013.01); *H01L 23/53295* (2013.01); *C01B 21/0828* (2013.01); *C07F 7/0803* (2013.01)

(56) References Cited

U.S. PATENT DOCUMENTS

| | | | |
|---|---|---|---|
| 2002/0001941 A1* | 1/2002 | Kudo | H01L 21/76808 438/633 |
| 2003/0190829 A1 | 10/2003 | Brennan | |
| 2005/0077628 A1* | 4/2005 | Kumar | H01L 21/76811 257/758 |
| 2008/0111238 A1 | 5/2008 | Wang et al. | |
| 2009/0230558 A1* | 9/2009 | Matsuoka | H01L 21/02063 257/773 |
| 2010/0102452 A1 | 4/2010 | Nakao | |
| 2015/0325525 A1 | 11/2015 | Singh | |

OTHER PUBLICATIONS

Garozzo et al., Fluorocarbon Chemistry: A 0-Dimensional Model for Oxide and Nitride Dry Etching, IEEE Transactions on Semiconductor Manufacturing, vol. 28, No. 3, Aug. 2015, pp. 337-344.

Ye-Jun et al., Study on the Hydrophobic Fluorinated Amorphous Carbon (a-C:F) Film Deposited by DBD-PECVD, Journal of Dalian Nationalities University, vol. 11, No. 1, Jan. 2009, pp. 45-50.

European Patent Application No. EP17207632.5, Extended European Search Report dated Jun. 1, 2018, 11 pages.

* cited by examiner

METHOD FOR FABRICATING DAMASCENE STRUCTURE USING FLUOROCARBON FILM

CROSS-REFERENCES TO RELATED APPLICATIONS

The present application claims priority to Chinese patent application No. 201611156276.4, filed with the State Intellectual Property Office of People's Republic of China on Dec. 15, 2016, the content of which is incorporated herein by reference in its entirety.

FIELD OF THE INVENTION

The present disclosure relates to semiconductor technology, and more particularly to an interconnect structure, a semiconductor device having the interconnect structure and manufacturing method thereof.

BACKGROUND OF THE INVENTION

With the development of integrated circuit technology, the feature sizes of semiconductor devices are getting smaller and smaller. In order to reduce parasitic capacitance between metal interconnect lines, a low-k dielectric material is gradually used instead of silicon dioxide in the interconnect structure. A porous ultra-low-k material can further reduce the dielectric constant of a dielectric material in the interconnect structure, so that porous ultra-low-k materials are used in interconnect structures in smaller-sized devices.

BRIEF SUMMARY OF THE INVENTION

The present inventor has discovered that, when a porous ultra-low-k material is used as the dielectric material in an interconnect structure, the porous ultra-low-k material may be affected by other processes. For example, a planarization process may be carried out after a metal layer is filled in a formed recess and through-holes. The planarization process may introduce water into the porous ultra-low-k material, thereby affecting the dielectric properties and reliability of the interconnect structure. The present disclosure provides a novel interconnect structure and method for manufacturing the same that can improve the reliability of the interconnect structure.

According to some embodiments of the present disclosure, a method for manufacturing an interconnect structure may include providing a metal interconnect layer, forming a dielectric layer on the metal interconnect layer, forming a fluorocarbon layer on the dielectric layer, forming a patterned hardmask layer on the fluorocarbon layer, etching the fluorocarbon layer and the dielectric layer using the patterned hardmask layer as a mask to form a trench in the dielectric layer and a through-hole through the dielectric layer to the metal interconnect layer, forming a metal layer filling the trench and the through-hole, and planarizing the metal layer until the planarized metal layer has an upper surface that is flush with an upper surface of the fluorocarbon layer.

In one embodiment, the patterned hardmask layer includes a first opening extending into the hardmask layer. In one embodiment, etching the fluorocarbon layer and the dielectric layer using the hardmask layer as the mask includes forming a patterned first mask layer on the hardmask layer, the patterned first mask layer having a second opening extending to a bottom of the first opening, etching the patterned hardmask layer, the fluorocarbon layer, and the dielectric layer using the first mask layer as a mask to form a third opening in the dielectric layer, removing the first mask layer, removing a portion of the dielectric layer below the third opening using the hardmask layer as a mask, and removing a portion of the hardmask layer, a portion of the fluorocarbon layer, and a portion of the dielectric layer below the first opening to form the trench and the through-hole.

In one embodiment, the first mask layer includes two second openings each extending to the bottom of the first opening to form two through-holes extending to the metal interconnect layer.

In one embodiment, forming the patterned hardmask layer on the fluorocarbon layer includes forming a first hardmask layer on the fluorocarbon layer, forming a second hardmask layer on the first hardmask layer, forming a third hardmask layer on the second hardmask layer, forming a second mask layer on the third hardmask layer, etching the third hardmask layer and the second hardmask layer using the second mask layer as a mask to form the first opening extending into the second hardmask layer or extending through the second hardmask layer to the first hardmask layer, and removing the second mask layer.

In one embodiment, forming the second mask layer on the third hardmask layer includes forming a mask oxide layer on the third hardmask layer, forming the second mask layer on the mask oxide layer. Etching the third hardmask layer and the second hardmask layer using the second mask layer as a mask includes etching the mask oxide layer, the third hardmask layer, and the second hardmask layer using the second mask layer as a mask, the method may further include, after removing the second mask layer, removing the mask oxide layer.

In one embodiment, the first hardmask layer includes non-porous SiOCH, the second hardmask layer includes TEOS, and the third hardmask layer includes TiN.

In one embodiment, the method may further include, prior to forming the metal layer, performing a heat treatment to remove moisture in the dielectric layer. In one embodiment, the heat treatment is performed at a temperature in a range between 100° C. and 400° C., and with at least one of nitrogen gas ($N_2$), ammonia gas ($NH_3$), and hydrazine gas ($N_2H_4$) as a protective gas.

In one embodiment, the method may further include forming a SiCN layer on the planarized metal layer and on the upper surface of the fluorocarbon layer.

In one embodiment, the dielectric layer includes a porous low-k dielectric layer. In one embodiment, the dielectric layer includes a SiCN layer on the metal interconnect layer, a buffer layer on the SiCN layer, and the porous low-k dielectric layer on the buffer layer.

In one embodiment, the fluorocarbon layer is a hydrogen-containing fluorocarbon layer. In one embodiment, the fluorocarbon layer has a thickness in a range between 5 angstroms and 1000 angstroms.

Embodiments of the present disclosure also provide an interconnect structure. The interconnect structure includes a metal interconnect layer, a dielectric layer on the metal interconnect layer, a fluorocarbon layer on the dielectric layer, a metal interconnect extending through the fluorocarbon layer and the dielectric layer to the metal interconnect layer, the metal interconnect including a first portion extending through the fluorocarbon layer and into an upper portion of the dielectric layer and a second portion below the first portion and extending through a lower portion of the dielectric layer to the metal interconnect layer.

In one embodiment, the second portion of the dielectric layer below the first portion includes two portions.

In one embodiment, the metal interconnect has an upper surface flush with an upper surface of the fluorocarbon layer. The interconnect structure further includes a SiCN layer on the upper surface of the metal interconnect and on the upper surface of the fluorocarbon layer.

In one embodiment, the dielectric layer includes a porous low-k dielectric layer. In one embodiment, the dielectric layer includes a SiCN layer on the metal interconnect layer, a buffer layer on the SiCN layer, and the porous low-k dielectric layer on the buffer layer.

In one embodiment, the fluorocarbon layer is a hydrogen-containing fluorocarbon layer. In one embodiment, the fluorocarbon layer has a thickness in a range between 5 angstroms and 1000 angstroms.

The following detailed description together with the accompanying drawings will provide a better understanding of the nature and advantages of the present invention.

BRIEF DESCRIPTION OF THE DRAWINGS

Embodiments of the present invention are described with reference to the accompanying drawings. In the drawings, like reference numbers may indicate identical or functionally similar elements.

DETAILED DESCRIPTION OF THE INVENTION

Figure 1:
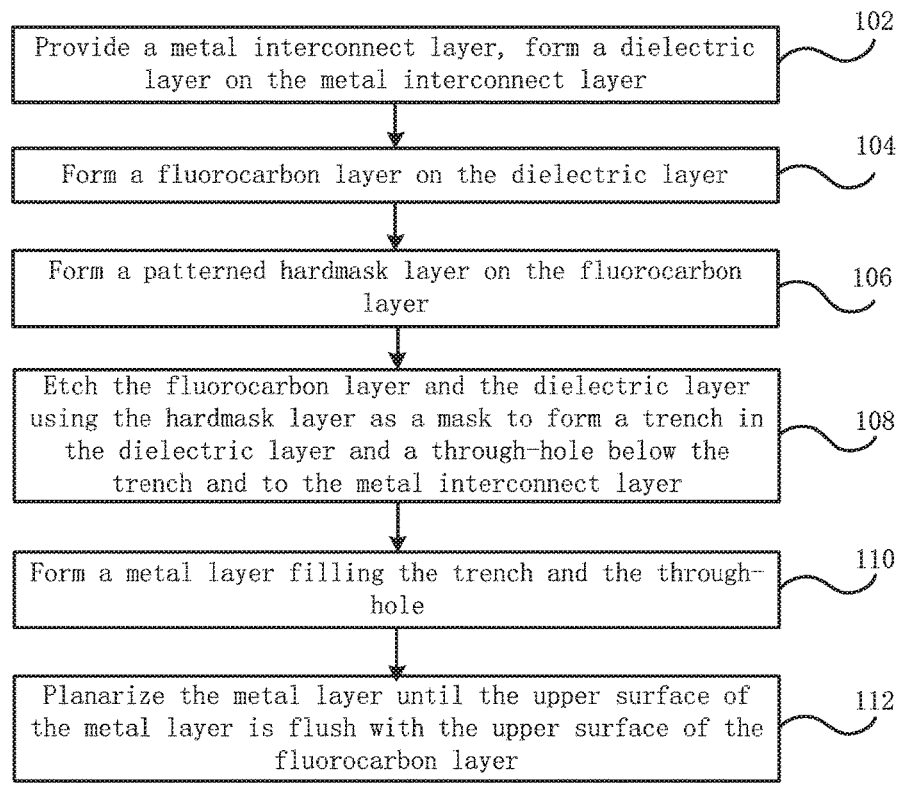
FIG. 1 is a simplified flowchart illustrating a method of manufacturing an interconnect structure according to an embodiment of the present invention.

Embodiments of the present invention now will be described more fully hereinafter with reference to the accompanying drawings. The invention may, however, be embodied in many different forms and should not be construed as limited to the embodiments set forth herein. Rather, these embodiments are provided so that this disclosure will be thorough and complete, and will fully convey the scope of the invention to those skilled in the art. The features may not be drawn to scale, some details may be exaggerated relative to other elements for clarity. Like numbers refer to like elements throughout.

It will be understood that when an element such as a layer, region or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "lateral" or "vertical" may be used herein to describe a relationship of one element, layer or region to another element, layer or region as illustrated in the figures. It will be understood that these terms are intended to encompass different orientations of the device in addition to the orientation depicted in the figures.

The terminology used herein is for the purpose of describing particular embodiments only and is not intended to be limiting of the invention. As used herein, the singular forms "a", "an", and "the" are intended to include the plural forms as well, unless the context clearly indicates otherwise. It will be further understood that the terms "comprises", "comprising", "includes", and/or "including" when used herein, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-sectional illustrations that are schematic illustrations of idealized embodiments (and intermediate structures) of the invention. The thickness of layers and regions in the drawings may be enlarged relative to other layers and regions for clarity. Additionally, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a discrete change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the invention.

The embodiments described and references in the disclosure to "one embodiment," "an embodiment," "an exemplary embodiment" indicate that the embodiments described may include a particular feature, structure, or characteristic. However, every embodiment may not necessary include the particular feature, structure or characteristic. As used throughout this disclosure, the terms "depositing" and "forming" are used interchangeably.

Embodiments of the present invention now will be described more fully hereinafter with reference to the accompanying drawings, in which embodiments of the invention are shown. This invention may, however, be embodied in many different forms and should not be construed as limited to the embodiments set forth herein.

Embodiments of the present invention propose the use of fluorocarbons to form interconnect structures. Fluorocarbons have good thermal stability and can withstand thermal shock in the integrated circuit manufacturing processes and increased temperature of integrated circuits during operation. In addition, fluorocarbons have good adhesion and good hole filling properties, and are compatible with manufacturing processes of integrated circuits.

FIG. 1 is a simplified flowchart illustrating a method of manufacturing an interconnect structure according to an embodiment of the present invention. Referring to FIG. 1, the method may include the following steps:

Step 102: providing a metal interconnect layer, and forming a dielectric layer on the metal interconnect layer. The metal interconnect layer may include copper. The dielectric layer may include a porous low-k dielectric material, e.g., SiCOH.

Step 104: forming a fluorocarbon layer on the dielectric layer by deposition. For example, the fluorocarbon layer may be formed using a plasma enhanced chemical vapor deposition (PECVD) process or a physical vapor deposition (PVD) process. The fluorocarbon layer may include a fluorocarbon compound having a chemical structure of $C_xF_y$, where x and y are integers that vary according to different process conditions. In one embodiment, the fluorocarbon layer may include a hydrogen-containing fluorocarbon layer.

Step 106: forming a patterned hardmask layer on the fluorocarbon layer.

Step 108: etching the fluorocarbon layer and the dielectric layer using the patterned hardmask layer as a mask to form a trench in the dielectric layer and a through-hole below the trench and extending to the metal interconnect layer.

Step 110: forming a metal layer by deposition to fill the trench and the through-hole. The metal layer may include copper.

Step 112: performing a planarization (e.g., chemical mechanical polishing) process on the metal layer so that the planarized metal layer has an upper surface that is substantially flush with the upper surface of the fluorocarbon layer. As used herein, the term "the surfaces are substantially flush with each other" means that the surfaces are coplanar or flush within the process variation tolerance.

According to embodiments of the present invention, a fluorocarbon layer is formed on a dielectric layer to prevent water from entering into the dielectric layer when planarizing a metal layer, thereby improving the reliability of the interconnect structure. Further, the fluorocarbon layer may also improve the interface property between a subsequent formed barrier layer (e.g., SiCN) and the dielectric layer and mitigate or avoid plasma damage to the dielectric layer in the process of forming the SiCN barrier layer, thereby improving the reliability of the interconnect structure.

FIGS. 2 to 9 are cross-sectional views illustrating intermediate stages of an interconnect structure in a manufacturing method according to some embodiments of the present invention. A manufacturing method of an interconnect structure according to some embodiments of the present invention will be described in detail with reference to FIGS. 2 to 9.

Figure 2:
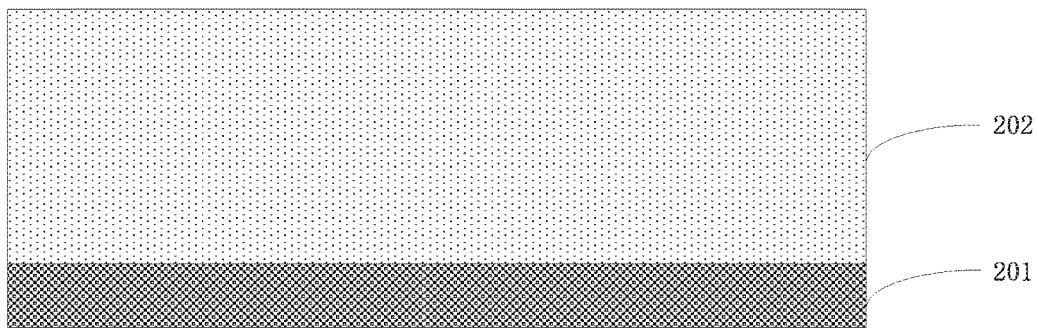
FIGS. 2 to 9 are cross-sectional views illustrating intermediate stages of an interconnect structure in a manufacturing method according to some embodiments of the present invention.

Referring to FIG. 2, a metal interconnect layer 201 is provided. A dielectric layer 202 is formed on the metal interconnect layer. In one embodiment, dielectric layer 202 may be a porous low-k or porous ultra-low-k dielectric layer having a k value less than 2.7. In another embodiment, dielectric layer 202 may include a SiCN layer on metal interconnect layer 201, a buffer layer (e.g., a silicon oxide layer) on the SiCN layer, and a porous low-k or porous ultra-low-k dielectric layer on the buffer layer. The porous low-k or porous ultra-low-k dielectric layer may include SiOCH.

Figure 3:
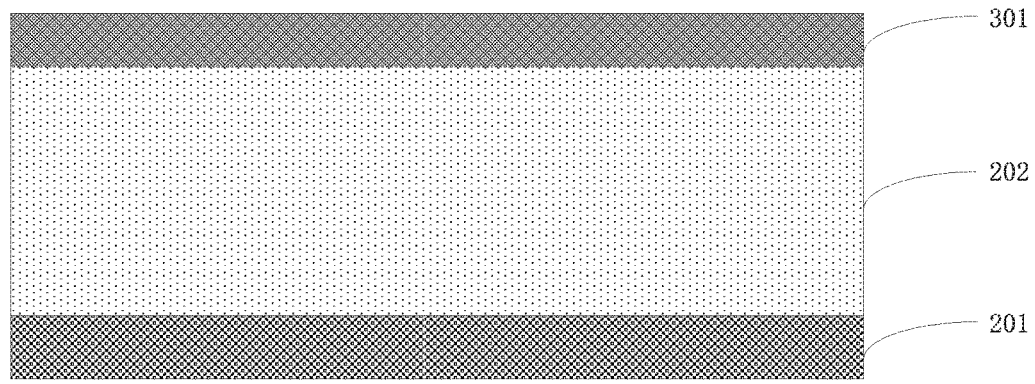

Referring to FIG. 3, a fluorocarbon layer 301 is formed on dielectric layer 202. For example, a fluorocarbon layer may be deposited by a PECVD or PVD process using organic gases containing carbon, fluorine, and hydrogen (e.g., $C_xF_y$ and $CH_4$) as a source gas. In one embodiment, fluorocarbon layer 301 may be a hydrogen-containing fluorocarbon layer. In one embodiment, fluorocarbon layer 301 may be a doped fluorocarbon layer, for example, the fluorocarbon layer may be doped with nitrogen or boron. In one embodiment, fluorocarbon layer 301 has a thickness in the range between 5 angstroms and 1000 angstroms, e.g., e.g., 50 angstroms, 100 angstroms, 400 angstroms, 600 angstroms, etc.

Figure 4:
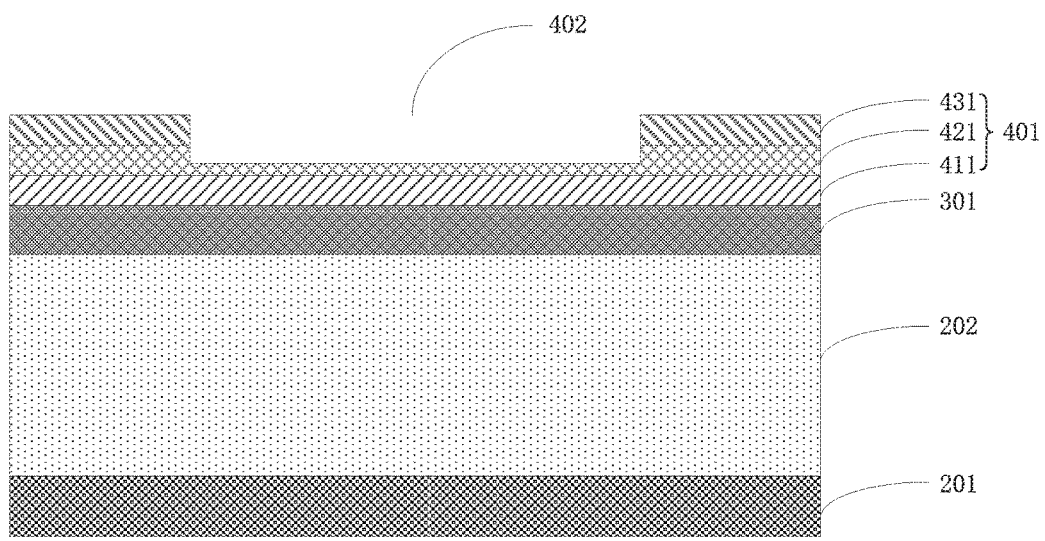

Next, referring to FIG. 4, a patterned hardmask layer 401 is formed on fluorocarbon layer 301. In one embodiment, patterned hardmask layer 401 has a first opening 402 extending into hardmask layer 401.

In some embodiments, a first hardmask layer 411 is formed on fluorocarbon layer 301, a second hardmask layer 421 is formed on first hardmask layer 411, and a third hardmask layer 431 is formed on second hardmask layer 421. In one embodiment, first hardmask layer 411 may include non-porous SiOCH; second hardmask layer 421 may include ethyl orthosilicate (TEOS); third hardmask layer 431 may include titanium nitride (TiN). Of course, the present invention is not limited thereto. Then, a patterned mask layer (not shown), e.g., a photoresist, is formed on third hardmask layer 431. In order to distinguish a subsequently formed first mask layer, the patterned mask layer herein is referred to as a second mask layer. Next, an etch process is performed on third hardmask layer 431 and second hardmask layer 421 using the second mask layer as a mask to form first opening 402 extending through third hardmask layer 431 into second hardmask layer 421 (as shown in FIG. 4) or to a surface of first hardmask layer 411. In one embodiment, first opening 402 may extend below the middle position relative to the upper surface of second hardmask layer 421, i.e., more than one half of the thickness of second hardmask layer 421 is removed. Thereafter, the second mask layer is removed to form first opening 402.

In some other embodiments, after sequentially forming first hardmask layer 411 on fluorocarbon layer 301, second hardmask layer 421 on first hardmask layer 411, and third hardmask layer 431 on second hardmask layer 421, a mask oxide layer (not shown), such as a silicon oxide layer, may be formed on third hardmask layer 431. Then, the second mask layer is formed on the mask oxide layer. The mask oxide layer, third mask layer 431 and second hardmask layer 421 are subsequently etched using the second mask layer as a mask. The second mask layer is then removed. Thereafter, the remaining portion of the mask oxide layer is removed to form first opening 402.

Next, fluorocarbon layer 301 and dielectric layer 202 are etched using hardmask layer 401 as a mask to form a trench in dielectric layer 202 and a through-hole below the trench and extending to a surface of metal interconnect layer 201.

It should be noted that, as used herein, the term "opening/through-hole/trench to a layer" means that the opening/through-hole/trench extends to the layer.

Figure 5:
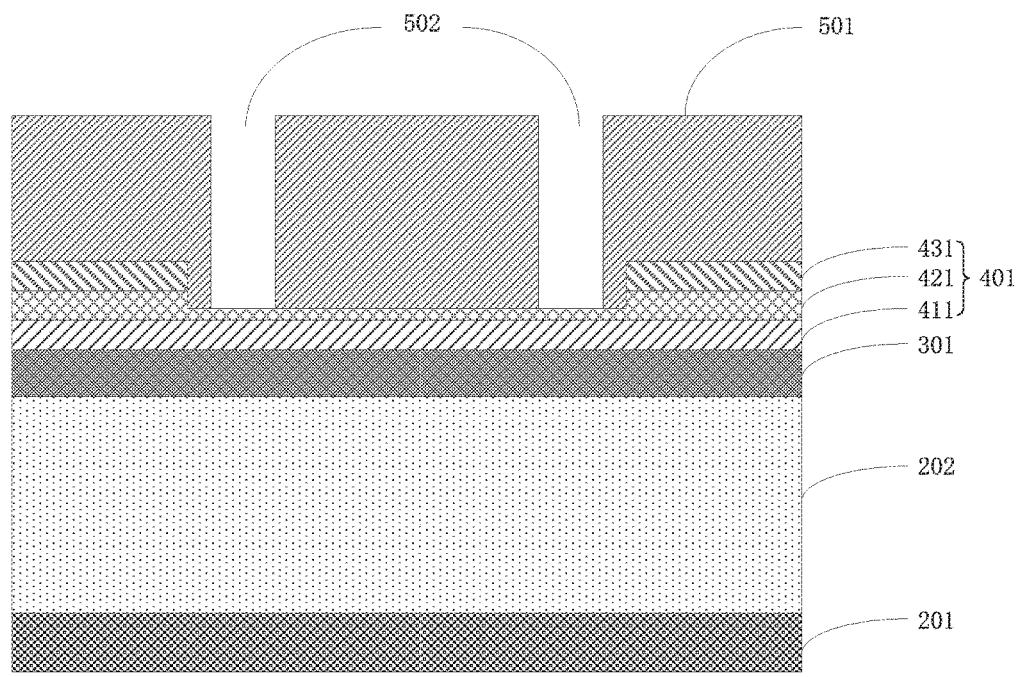
Figure 6:
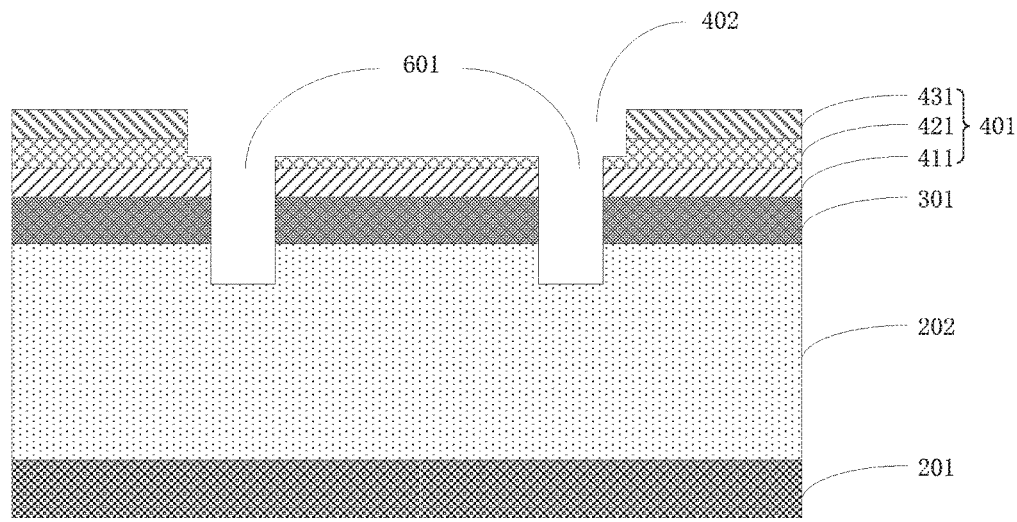
Figure 7:
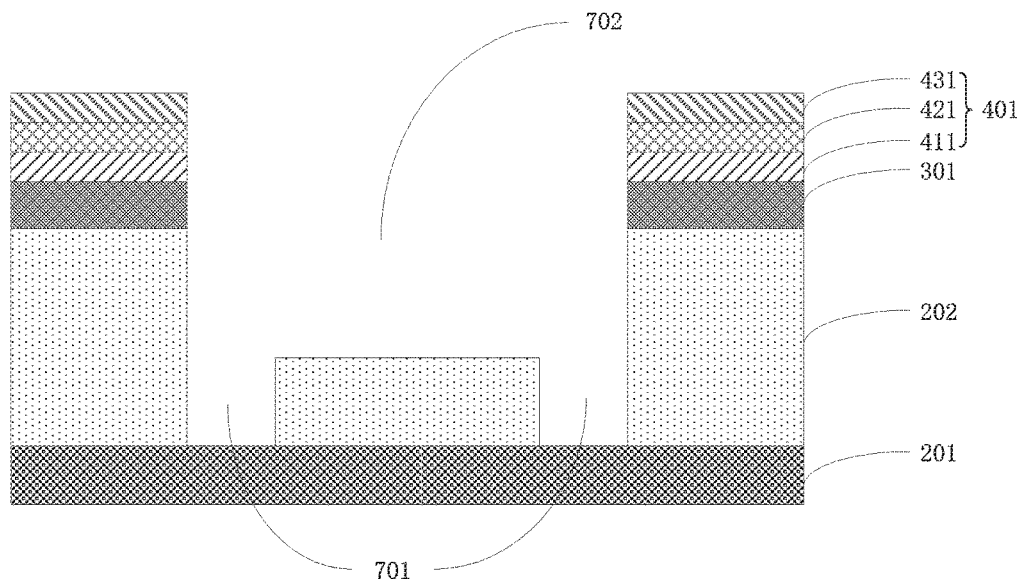

In one embodiment, the trench in dielectric layer 202 and the through-hole to metal interconnect layer 201 may be formed by process steps with reference to FIGS. 5 to 7.

Referring to FIG. 5, a patterned mask layer 501 (also referred to as a first mask layer), e.g., a photoresist, is formed on hardmask layer 401. Mask layer 501 has a second opening 502 extending to the bottom of first opening 402. In one embodiment, patterned mask layer 501 (i.e., the first mask layer) may have two openings 502 extending to the bottom of first opening 402 (as shown in FIG. 5), so that two through-holes can subsequently be formed to metal interconnect layer 201. In another embodiment, first mask layer 501 may have a second opening 502 extending to the bottom of first opening 402 such that a through-hole can subsequently be formed to metal interconnect layer 201.

Referring to FIG. 6, hardmask layer 401, fluorocarbon layer 301, dielectric layer 202 are etched using first mask layer 501 as a mask to form a third opening 601 in dielectric layer 202. Thereafter, first mask layer 501 is removed.

Referring to FIG. 7, a portion of dielectric layer 202 below a remaining portion of hardmask layer 401 is removed using the remaining portion of hardmask layer 401 as a mask, and removing a portion of hardmask layer 401 (e.g., the remaining second hardmask layer 421 and first hardmask layer 411), a portion of fluorocarbon layer 301, and a portion of dielectric layer 301 below first opening 402 to form a trench 702 in dielectric layer 202 and a through-hole 701 below trench 702 and extending to metal interconnect layer 201.

It is understood that the number of through-holes 701 can be any integer number. In the example shown in FIG. 7, two through-holes 701 are used below trench 702 and extending through the remaining portion of dielectric layer 202 to metal interconnect layer 201. But it is understood that the number is arbitrary chosen for describing the example embodiment and should not be limiting. In some other embodiments, the number of through-holes 701 may be one.

Figure 8:
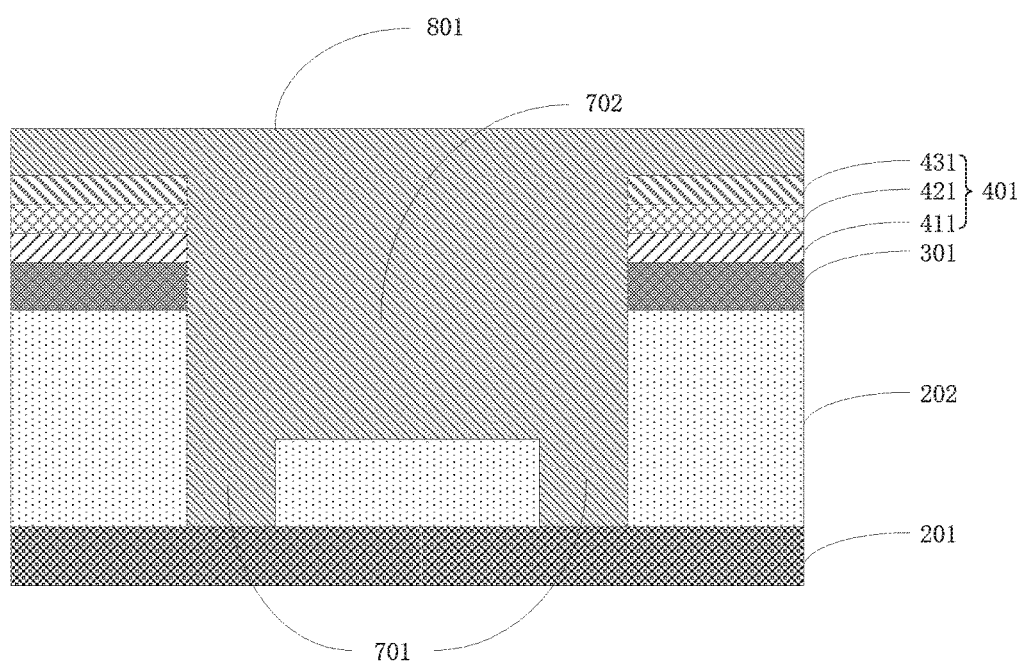

After forming trench 702 and through-hole 701, a metal layer 801 is formed by deposition to fill trench 702 and through-hole 701, as shown in FIG. 8. Metal layer 801 also covers a remaining portion of hardmask layer 401. In one embodiment, metal layer 801 may include copper.

In one embodiment, prior to forming metal layer 801, a heat treatment may be performed to remove moisture from dielectric layer 202. In one embodiment, a heat treatment may be performed at a temperature in the range between 100° C. and 400° C. (e.g., 200° C., 300° C.), and with at least one of nitrogen gas ($N_2$), ammonia gas ($NH_3$), and hydrazine gas ($N_2H_4$) as a protective gas. After the heat treatment, the moisture in the dielectric layer substantially disappears, and in the subsequent planarization process, water will not enter the dielectric layer due to the protection of fluorocarbon layer 301.

Figure 9:
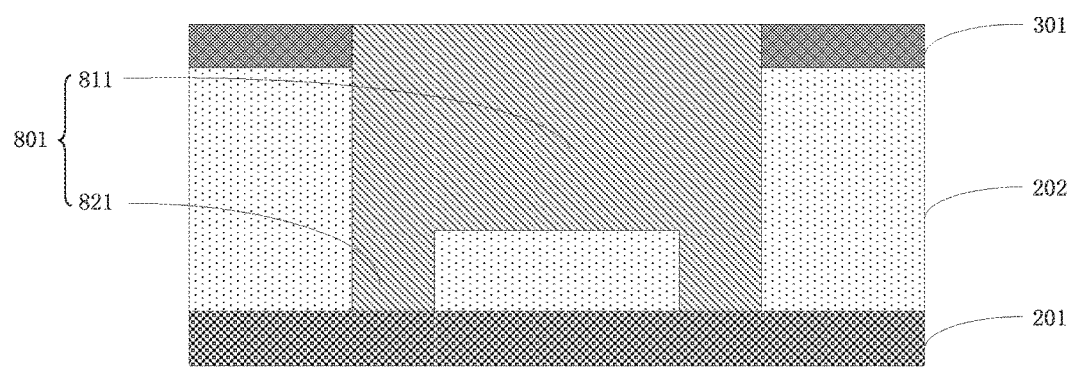

Next, a planarization (e.g., a chemical mechanical polishing) process is performed on metal layer 801, so that the planarized metal layer (also referred to as metal interconnect) 801 has upper surface that is substantially flush with the upper surface of the remaining portion of fluorocarbon layer 301, as shown in FIG. 9. Metal interconnect 801 includes a first portion 811 and a second portion 821 below first portion 811. First portion 811 is formed by the portion of the metal layer filling the trench, and second portion 821 is formed by the portion the metal layer filling the through-hole. Fluorocarbon layer 301 on dielectric layer can prevent water from entering dielectric layer 202 in the planarization process, thereby improving the reliability of the interconnect structure.

Next, in one embodiment, a SiCN barrier layer may be formed on the planarized surface of metal layer 801 and on the upper surface of fluorocarbon layer 301. Fluorocarbon layer 301 may also improves the interface performance between the SiCN barrier layer and dielectric layer 202 and may mitigate or avoid plasma damage to the dielectric layer in the process of forming the SiCN barrier layer, and further improve the reliability of the interconnect structure.

A method for manufacturing an interconnect structure according to some embodiments of the present disclosure has been described above in connection with FIGS. 2 to 9. It should be understood that certain steps in FIGS. 2 to 9 may be performed in different embodiments, and certain steps are not necessarily in one embodiment.

Embodiments of the present disclosure also provide an interconnect structure. Referring to FIG. 9, the interconnect structure may include a metal interconnect layer 201, a dielectric layer 202 on metal interconnect 201, a fluorocarbon layer 301 on dielectric layer 202, and a metal interconnect 801 on metal interconnect layer 201 and extending through fluorocarbon layer 301 and dielectric layer 202. Metal interconnect 801 includes a first portion 811 and a second portion 821 adjacent and below first portion 811. First portion 811 extends through fluorocarbon layer 301 and an upper portion of dielectric layer 202, and second portion 821 extends through a lower portion of dielectric layer 202 and in contact with metal interconnect layer 201. In one embodiment, metal interconnect 801 may include a first portion 811 and two second portion 821 disposed below first portion 811.

It is to be understood that the terms "upper portion" and "lower portion" of dielectric layer 202 are merely conceptual. For example, a predetermined horizontal position of dielectric layer 202 is defined as a dividing line (a virtual separation line), the portion of dielectric layer 202 above the dividing line is referred to as the upper portion, and the portion of dielectric layer 202 below the dividing line is referred to as the lower portion of dielectric layer 202.

In some other embodiments, the interconnect structure may also include a SiCN layer on metal interconnect 801 and on fluorocarbon layer 301.

The foregoing descriptions of specific embodiments of the present invention have been presented for purpose of illustration and description. They are not intended to be exhaustive or to limit the invention to the precise forms disclosed, and obviously many modifications and variations are possible in light of the above disclosure. The exemplary embodiment has been described in order to best explain the principles of the invention and its practical application. Many embodiments will be apparent to those of skill in the art upon reviewing the above description. The scope of the invention should, therefore, be determined not with reference to the above description, but instead should be determined with reference to the appended claims along with their full scope of equivalents.

What is claimed is:

1. A method for manufacturing an interconnect structure, the method comprising:
   providing a metal interconnect layer;
   forming a dielectric layer on the metal interconnect layer;
   forming a doped fluorocarbon layer on the dielectric layer;
   forming a patterned hardmask layer on the doped fluorocarbon layer, wherein the patterned hardmask layer comprises:
   a first hardmask layer comprising non-porous SiOCH on the doped fluorocarbon layer;
   a second hardmask layer comprising TEOS on the first hardmask layer;
   a third hardmask layer comprising TiN on the second hardmask layer;
   etching the doped fluorocarbon layer and the dielectric layer using the patterned hardmask layer as a mask to form a trench in the dielectric layer and a through-hole through the dielectric layer to the metal interconnect layer;
   forming a metal layer filling the trench and the through-hole; and
   planarizing the metal layer until the planarized metal layer has an upper surface that is flush with an upper surface of the doped fluorocarbon layer.

2. The method of claim 1, wherein the patterned hardmask layer comprises a first opening extending into the hardmask layer, and etching the doped fluorocarbon layer and the dielectric layer using the hardmask layer as the mask comprises:

forming a patterned first mask layer on the hardmask layer, the patterned first mask layer having a second opening extending to a bottom of the first opening;

etching the patterned hardmask layer, the doped fluorocarbon layer, and the dielectric layer using the first mask layer as a mask to form a third opening in the dielectric layer;

removing the first mask layer;

removing a portion of the dielectric layer below the third opening using the hardmask layer as a mask; and removing a portion of the hardmask layer, a portion of the doped fluorocarbon layer, and a portion of the dielectric layer below the first opening to form the trench and the through-hole.

3. The method of claim 2, wherein the first mask layer comprises two second openings each extending to the bottom of the first opening to form two through-holes extending to the metal interconnect layer.

4. The method of claim 2, wherein forming the patterned hardmask layer on the doped fluorocarbon layer comprises:

forming a second mask layer on the third hardmask layer;

etching the third hardmask layer and the second hardmask layer using the second mask layer as a mask to form the first opening extending into the second hardmask layer or extending through the second hardmask layer to the first hardmask layer; and removing the second mask layer.

5. The method of claim 4, wherein forming the second mask layer on the third hardmask layer comprises:

forming a mask oxide layer on the third hardmask layer;

forming the second mask layer on the mask oxide layer; and wherein etching the third hardmask layer and the second hardmask layer using the second mask layer as a mask comprises:

etching the mask oxide layer, the third hardmask layer, and the second hardmask layer using the second mask layer as a mask;

the method further comprising, after removing the second mask layer:

removing the mask oxide layer.

6. The method of claim 1, further comprising, prior to forming the metal layer:

performing a heat treatment to remove moisture in the dielectric layer.

7. The method of claim 6, wherein the heat treatment is performed at a temperature in a range between 100° C. and 400° C., and with at least one of nitrogen gas, ammonia gas, and hydrazine gas as a protective gas.

8. The method of claim 1, further comprising:

forming a SiCN layer on the planarized metal layer and on the upper surface of the doped fluorocarbon layer.

9. The method of claim 1, wherein the dielectric layer comprises a porous low-k dielectric layer.

10. The method of claim 1, wherein the dielectric layer comprises a SiCN layer on the metal interconnect layer, a buffer layer on the SiCN layer, and a porous low-k dielectric layer on the buffer layer.

11. The method of claim 1, wherein the doped fluorocarbon layer is a hydrogen-containing fluorocarbon layer.

12. The method of claim 1, wherein the doped fluorocarbon layer has a thickness in a range between 5 angstroms and 1000 angstroms.

13. The method of claim 1, wherein the doped fluorocarbon layer contains nitrogen.

14. The method of claim 1, wherein the doped fluorocarbon layer contains boron.

* * * * *